(12) United States Patent
Spignesi Jr. et al.

(10) Patent No.: US 9,280,863 B2
(45) Date of Patent: Mar. 8, 2016

(54) AUTOMATED DISPENSING SYSTEM FOR PHARMACEUTICALS AND OTHER MEDICAL ITEMS

(75) Inventors: Robert G. Spignesi Jr., Raleigh, NC (US); Mark Longley, Raleigh, NC (US)

(73) Assignee: Parata Systems, LLC, Durham, NC (US)

(*) Notice: Subject to any disclaimer, the term of this patent is extended or adjusted under 35 U.S.C. 154(b) by 1669 days.

(21) Appl. No.: 12/502,542

(22) Filed: Jul. 14, 2009

(65) Prior Publication Data

US 2010/0017296 A1   Jan. 21, 2010

Related U.S. Application Data

(60) Provisional application No. 61/081,129, filed on Jul. 16, 2008.

(51) Int. Cl.
| | |
|---|---|
| G07F 17/00 | (2006.01) |
| G06F 19/00 | (2011.01) |
| G07F 7/00 | (2006.01) |
| G07F 11/00 | (2006.01) |
| G07F 11/44 | (2006.01) |

(52) U.S. Cl.
CPC ........ G07F 17/0092 (2013.01); G06F 19/3462 (2013.01); G07F 7/00 (2013.01); G07F 11/002 (2013.01); G07F 11/44 (2013.01)

(58) Field of Classification Search
CPC .................................................. G07F 17/0092
See application file for complete search history.

(56) References Cited

U.S. PATENT DOCUMENTS

| | | |
|---|---|---|
| 3,732,544 A | 5/1973 | Obland |
| 3,786,421 A | 1/1974 | Wostl et al. |
| 3,903,773 A | 9/1975 | Furukawa |
| 3,941,977 A | 3/1976 | Voss et al. |
| 3,943,355 A | 3/1976 | Kinker et al. |
| 4,130,881 A | 12/1978 | Haessler et al. |
| 4,223,751 A | 9/1980 | Ayers et al. |
| 4,359,631 A | 11/1982 | Lockwood et al. |
| 4,519,522 A | 5/1985 | McElwee |
| 4,546,901 A | 10/1985 | Buttarazzi |
| 4,636,634 A | 1/1987 | Harper et al. |
| 4,791,411 A | 12/1988 | Staar |

(Continued)

FOREIGN PATENT DOCUMENTS

| | | |
|---|---|---|
| EP | 0 656 200 A2 | 6/1995 |
| WO | WO 01/84444 | 11/2001 |

(Continued)

OTHER PUBLICATIONS

International Search Report and the Written Opinion of PCT/US2009/004092 mailed Oct. 29, 2009.

*Primary Examiner* — Timothy Waggoner
(74) *Attorney, Agent, or Firm* — Myers Bigel & Sibley, P.A.

(57) ABSTRACT

A system for dispensing a plurality of customized doses of pharmaceuticals includes: a housing; a customer interaction station; a customized packaging station configured to selectively package individual doses of medication into customized packaging, the medications being selected responsive to input from the customer input station; and a controller connected to the customer interaction station and the customized packaging station, the controller configured to control the customized packaging based on customer input from the customer interaction station.

3 Claims, 2 Drawing Sheets

(56) References Cited

U.S. PATENT DOCUMENTS

| | | | |
|---|---|---|---|
| 4,812,629 A | 3/1989 | O'Neil et al. | |
| 4,814,592 A | 3/1989 | Bradt et al. | |
| 4,839,505 A | 6/1989 | Bradt et al. | |
| 4,846,367 A | 7/1989 | Guigan et al. | |
| 4,858,743 A | 8/1989 | Paraskevakos et al. | |
| 4,866,255 A | 9/1989 | Sing | |
| 4,951,308 A | 8/1990 | Bishop et al. | |
| 4,995,498 A | 2/1991 | Menke | |
| 5,013,897 A | 5/1991 | Harman et al. | |
| 5,014,875 A | 5/1991 | McLaughlin et al. | |
| 5,020,958 A | 6/1991 | Tuttobene | |
| 5,025,426 A | 6/1991 | Blumberg et al. | |
| 5,036,472 A | 7/1991 | Buckley et al. | |
| 5,042,686 A | 8/1991 | Stucki | |
| 5,047,948 A | 9/1991 | Turner | |
| 5,088,586 A | 2/1992 | Isobe et al. | |
| 5,095,195 A | 3/1992 | Harman et al. | |
| 5,105,978 A | 4/1992 | Trouteaud et al. | |
| 5,113,351 A | 5/1992 | Bostic | |
| 5,139,384 A | 8/1992 | Tuttobene | |
| 5,150,817 A | 9/1992 | Livingston | |
| 5,159,560 A | 10/1992 | Newell et al. | |
| 5,172,829 A | 12/1992 | Dellicker, Jr. | |
| 5,193,855 A | 3/1993 | Shamos | |
| 5,212,649 A | 5/1993 | Pelletier et al. | |
| 5,223,829 A | 6/1993 | Watabe | |
| 5,231,272 A | 7/1993 | Mardon | |
| 5,239,459 A * | 8/1993 | Hunt et al. | 700/90 |
| 5,299,121 A | 3/1994 | Brill et al. | |
| 5,303,844 A | 4/1994 | Muehlberger | |
| 5,313,393 A | 5/1994 | Varley et al. | |
| 5,335,816 A | 8/1994 | Kaufman et al. | |
| 5,385,265 A | 1/1995 | Schlamp | |
| 5,390,711 A | 2/1995 | Murphey | |
| 5,408,443 A | 4/1995 | Weinberger | |
| 5,431,299 A | 7/1995 | Brewer et al. | |
| 5,438,523 A | 8/1995 | Humm et al. | |
| 5,445,294 A | 8/1995 | Gardner et al. | |
| 5,445,295 A | 8/1995 | Brown | |
| 5,468,110 A | 11/1995 | McDonald et al. | |
| 5,482,139 A | 1/1996 | Rivalto | |
| 5,499,707 A | 3/1996 | Steury | |
| 5,502,944 A | 4/1996 | Kraft et al. | |
| 5,533,645 A | 7/1996 | Wittern, Jr. et al. | |
| 5,594,638 A | 1/1997 | Iliff | |
| 5,597,995 A | 1/1997 | Williams et al. | |
| 5,660,176 A | 8/1997 | Iliff | |
| 5,678,393 A | 10/1997 | Yuyama et al. | |
| 5,713,485 A | 2/1998 | Liff et al. | |
| 5,713,648 A | 2/1998 | Geib et al. | |
| 5,720,154 A | 2/1998 | Lasher et al. | |
| 5,722,215 A | 3/1998 | Yuyama | |
| 5,724,968 A | 3/1998 | Iliff | |
| 5,728,999 A | 3/1998 | Teicher | |
| 5,746,232 A | 5/1998 | Dragotta | |
| 5,748,485 A | 5/1998 | Christiansen et al. | |
| 5,787,678 A | 8/1998 | Koike et al. | |
| 5,790,409 A | 8/1998 | Fedor et al. | |
| 5,797,515 A | 8/1998 | Liff et al. | |
| 5,797,839 A | 8/1998 | Herscu | |
| 5,812,410 A | 9/1998 | Lion et al. | |
| 5,838,575 A * | 11/1998 | Lion | 700/231 |
| 5,839,257 A | 11/1998 | Soderstrom et al. | |
| 5,839,836 A | 11/1998 | Yuyama et al. | |
| 5,845,255 A | 12/1998 | Mayaud | |
| 5,852,670 A | 12/1998 | Setlak et al. | |
| 5,875,610 A | 3/1999 | Yuyama et al. | |
| 5,880,443 A | 3/1999 | McDonald et al. | |
| 5,883,806 A | 3/1999 | Meador et al. | |
| 5,893,697 A | 4/1999 | Zini et al. | |
| 5,905,653 A | 5/1999 | Higham et al. | |
| 5,930,766 A | 7/1999 | Gibb | |
| 5,935,060 A | 8/1999 | Iliff | |
| 5,945,651 A | 8/1999 | Chorosinski et al. | |
| 5,963,136 A | 10/1999 | O'Brien | |
| 5,970,462 A | 10/1999 | Reichert | |
| 5,971,593 A | 10/1999 | McGrady | |
| 5,971,594 A | 10/1999 | Sahai et al. | |
| 6,003,006 A | 12/1999 | Colella et al. | |
| 6,010,064 A | 1/2000 | Umeda et al. | |
| 6,019,249 A | 2/2000 | Michael et al. | |
| 6,021,211 A | 2/2000 | Setlak et al. | |
| 6,021,392 A | 2/2000 | Lester et al. | |
| 6,024,699 A | 2/2000 | Surwit et al. | |
| 6,068,156 A | 5/2000 | Liff et al. | |
| 6,131,399 A | 10/2000 | Hall | |
| 6,152,364 A | 11/2000 | Schoonen et al. | |
| 6,161,059 A | 12/2000 | Tedesco et al. | |
| 6,170,230 B1 | 1/2001 | Chudy et al. | |
| 6,170,929 B1 | 1/2001 | Wilson et al. | |
| 6,199,720 B1 | 3/2001 | Rudick et al. | |
| 6,206,829 B1 | 3/2001 | Iliff | |
| 6,219,587 B1 | 4/2001 | Ahlin et al. | |
| 6,230,927 B1 | 5/2001 | Schoonen et al. | |
| 6,230,930 B1 | 5/2001 | Sorensen et al. | |
| 6,234,964 B1 | 5/2001 | Iliff | |
| 6,256,967 B1 | 7/2001 | Hebron et al. | |
| 6,270,456 B1 | 8/2001 | Iliff | |
| 6,308,494 B1 * | 10/2001 | Yuyama et al. | 53/154 |
| 6,324,520 B1 | 11/2001 | Walker et al. | |
| 6,330,491 B1 | 12/2001 | Lion | |
| 6,350,239 B1 | 2/2002 | Ohad et al. | |
| 6,352,200 B1 | 3/2002 | Schoonen et al. | |
| 6,354,498 B1 | 3/2002 | Lutz | |
| 6,370,841 B1 | 4/2002 | Chudy et al. | |
| 6,383,135 B1 | 5/2002 | Chikovani et al. | |
| 6,397,126 B1 | 5/2002 | Nelson | |
| 6,397,193 B1 | 5/2002 | Walker et al. | |
| 6,407,665 B2 | 6/2002 | Maloney | |
| 6,416,270 B1 | 7/2002 | Steury et al. | |
| 6,433,684 B1 | 8/2002 | Lie | |
| 6,449,627 B1 | 9/2002 | Baer et al. | |
| 6,449,927 B2 | 9/2002 | Hebron et al. | |
| 6,457,038 B1 | 9/2002 | Defosse | |
| 6,464,142 B1 | 10/2002 | Denenberg et al. | |
| 6,468,210 B1 | 10/2002 | Iliff | |
| 6,475,143 B2 | 11/2002 | Iliff | |
| 6,505,754 B1 | 1/2003 | Kenny et al. | |
| 6,522,772 B1 | 2/2003 | Morrison et al. | |
| 6,524,241 B2 | 2/2003 | Iliff | |
| 6,527,713 B2 | 3/2003 | Iliff | |
| 6,529,801 B1 | 3/2003 | Rosenblum | |
| 6,533,170 B1 | 3/2003 | Kit | |
| 6,535,637 B1 | 3/2003 | Wootton et al. | |
| 6,556,889 B2 | 4/2003 | Rudick et al. | |
| 6,564,121 B1 | 5/2003 | Wallace et al. | |
| 6,569,093 B2 | 5/2003 | Iliff | |
| 6,584,309 B1 | 6/2003 | Whigham | |
| 6,594,549 B2 | 7/2003 | Siegel | |
| 6,600,420 B2 | 7/2003 | Goff et al. | |
| 6,607,482 B1 | 8/2003 | Teitelbaum | |
| 6,648,649 B2 | 11/2003 | Rappaport | |
| 6,658,323 B2 * | 12/2003 | Tedesco et al. | 700/236 |
| 6,658,396 B1 | 12/2003 | Tang et al. | |
| 6,682,156 B2 | 1/2004 | Herrington | |
| 6,694,217 B2 | 2/2004 | Bloom | |
| 6,707,381 B1 | 3/2004 | Maloney | |
| 6,711,460 B1 * | 3/2004 | Reese | 700/244 |
| 6,711,465 B2 | 3/2004 | Tomassi | |
| 6,732,884 B2 | 5/2004 | Topliffe et al. | |
| 6,735,497 B2 | 5/2004 | Wallace et al. | |
| 6,764,445 B2 | 7/2004 | Iliff | |
| 6,771,369 B2 | 8/2004 | Rzasa et al. | |
| 6,871,783 B2 | 3/2005 | Kaafarani et al. | |
| 6,874,684 B1 | 4/2005 | Denenberg et al. | |
| 6,877,655 B1 | 4/2005 | Robertson et al. | |
| 6,892,941 B2 | 5/2005 | Rosenblum | |
| 6,925,783 B1 | 8/2005 | Pearson | |
| 6,935,560 B2 | 8/2005 | Andreasson et al. | |
| 6,945,457 B1 | 9/2005 | Barcelou | |
| 6,961,000 B2 | 11/2005 | Chung | |
| 6,994,409 B2 | 2/2006 | Godlewski | |
| 7,006,893 B2 | 2/2006 | Hart et al. | |
| 7,028,447 B2 | 4/2006 | Sung | |

(56) References Cited

U.S. PATENT DOCUMENTS

| | | | |
|---|---|---|---|
| 7,048,141 B2 | 5/2006 | Abdulhay et al. | |
| 7,059,098 B2 | 6/2006 | Kim | |
| 7,072,855 B1 | 7/2006 | Godlewski et al. | |
| 7,098,793 B2 | 8/2006 | Chung | |
| 7,123,989 B2 | 10/2006 | Pinney et al. | |
| 7,228,200 B2 | 6/2007 | Baker et al. | |
| 7,289,879 B2 | 10/2007 | William et al. | |
| 7,295,889 B2* | 11/2007 | Lahteenmaki | 700/233 |
| 7,311,666 B2 | 12/2007 | Stupp et al. | |
| 7,366,586 B2* | 4/2008 | Kaplan et al. | 700/241 |
| 7,451,583 B2* | 11/2008 | Kim | 221/154 |
| 7,454,880 B1 | 11/2008 | Austin et al. | |
| 7,469,213 B1 | 12/2008 | Rao | |
| 7,493,190 B1 | 2/2009 | Tomassi | |
| 7,523,594 B2 | 4/2009 | Greenwald et al. | |
| 7,689,318 B2 | 3/2010 | Draper | |
| 7,783,379 B2 | 8/2010 | Beane et al. | |
| 7,860,605 B2* | 12/2010 | Frankel | 700/236 |
| 2001/0028308 A1 | 10/2001 | De La Huerga | |
| 2001/0029405 A1 | 10/2001 | Lipps | |
| 2002/0004690 A1 | 1/2002 | Paulucci et al. | |
| 2002/0068857 A1 | 6/2002 | Iliff | |
| 2002/0143434 A1 | 10/2002 | Greeven et al. | |
| 2002/0187248 A1 | 12/2002 | Childers | |
| 2003/0028811 A1 | 2/2003 | Walker et al. | |
| 2003/0117281 A1 | 6/2003 | Sriharto et al. | |
| 2003/0130868 A1 | 7/2003 | Coelho | |
| 2003/0179287 A1 | 9/2003 | Kozic et al. | |
| 2003/0212471 A1 | 11/2003 | Chakravarti | |
| 2004/0019794 A1 | 1/2004 | Moradi et al. | |
| 2004/0050855 A1 | 3/2004 | Jurgenson | |
| 2004/0088187 A1 | 5/2004 | Chudy et al. | |
| 2004/0111277 A1 | 6/2004 | Pearson et al. | |
| 2004/0138921 A1 | 7/2004 | Broussard et al. | |
| 2004/0140317 A1 | 7/2004 | Forte | |
| 2004/0164864 A1 | 8/2004 | Chung et al. | |
| 2004/0199408 A1 | 10/2004 | Johnson | |
| 2004/0204954 A1 | 10/2004 | Lacko | |
| 2004/0210488 A1 | 10/2004 | Doherty | |
| 2005/0004700 A1 | 1/2005 | DiMaggio | |
| 2005/0021175 A1 | 1/2005 | Bain | |
| 2005/0023286 A1 | 2/2005 | Pinney et al. | |
| 2005/0049746 A1 | 3/2005 | Rosenblum | |
| 2005/0096785 A1 | 5/2005 | Moncrief et al. | |
| 2005/0102163 A1 | 5/2005 | Coughlin | |
| 2005/0125097 A1 | 6/2005 | Chudy et al. | |
| 2005/0144037 A1 | 6/2005 | Geiger | |
| 2005/0192705 A1 | 9/2005 | Pinney et al. | |
| 2005/0224510 A1 | 10/2005 | Remis et al. | |
| 2005/0288906 A1 | 12/2005 | Drennen, III et al. | |
| 2006/0020175 A1 | 1/2006 | Berry et al. | |
| 2006/0031097 A1 | 2/2006 | Lipscher et al. | |
| 2006/0088196 A1 | 4/2006 | Popovich, Jr. et al. | |
| 2006/0122465 A1 | 6/2006 | Bastien et al. | |
| 2006/0124656 A1 | 6/2006 | Popovich, Jr. | |
| 2006/0149140 A1 | 7/2006 | Eldridge | |
| 2006/0167719 A1 | 7/2006 | Kim | |
| 2006/0192652 A1 | 8/2006 | Mandava et al. | |
| 2006/0266823 A1 | 11/2006 | Passen et al. | |
| 2006/0272976 A1 | 12/2006 | Pinney et al. | |
| 2007/0093934 A1 | 4/2007 | Garneau, III | |
| 2008/0042843 A1 | 2/2008 | Kim | |
| 2008/0071648 A1 | 3/2008 | Kim | |
| 2008/0081955 A1 | 4/2008 | Eisenhandler et al. | |
| 2008/0081957 A1 | 4/2008 | Jung et al. | |
| 2008/0086326 A1 | 4/2008 | Moura et al. | |
| 2008/0091086 A1 | 4/2008 | Legere et al. | |
| 2008/0103626 A1 | 5/2008 | Frankel | |
| 2008/0189173 A1 | 8/2008 | Bakar et al. | |
| 2008/0262649 A1 | 10/2008 | Allinson | |
| 2008/0269947 A1 | 10/2008 | Beane et al. | |
| 2008/0271417 A1 | 11/2008 | Drost et al. | |
| 2008/0306761 A1 | 12/2008 | George et al. | |
| 2009/0125324 A1 | 5/2009 | Keravich et al. | |
| 2010/0010666 A1 | 1/2010 | Adams | |

FOREIGN PATENT DOCUMENTS

| | | |
|---|---|---|
| WO | WO 2004/021289 A3 | 3/2004 |
| WO | WO 2008/000790 | 1/2008 |
| WO | WO 2008/006203 A1 | 1/2008 |
| WO | WO 2008/089249 | 7/2008 |
| WO | WO 2009/007766 | 1/2009 |

* cited by examiner

AUTOMATED DISPENSING SYSTEM FOR PHARMACEUTICALS AND OTHER MEDICAL ITEMS

RELATED APPLICATION

This application claims priority from U.S. Provisional Patent Application No. 61/081,129, filed Jul. 16, 2008 and entitled AUTOMATED DISPENSING SYSTEM FOR PHARMACEUTICALS AND OTHER MEDICAL ITEMS, the disclosure of which is hereby incorporated herein in its entirety.

FIELD OF THE INVENTION

This application is directed generally to materials handling, and more particularly to machines for distributing items to customers.

BACKGROUND OF THE INVENTION

Automated pharmaceutical delivery systems have been in use for over thirty years. The initial purpose of such systems was to reduce the high rates of medication errors associated with manual distribution. In modern times, automated systems present more sophisticated advantages. These include: further reduction of errors, lower costs associated with pharmaceutical distribution, reduction of personnel, inventory control, automated documentation, and relieving professional pharmacists of many tasks.

Automated machines to distribute filled prescriptions to patients also exist. Exemplary machines are discussed in, for example, U.S. Patent Publication No. 20050021175 to Bain; U.S. Pat. No. 7,228,200 to Baker et al.; U.S. Pat. No. 7,537,155 to Denenberg; and U.S. Pat. No. 7,123,989 to Pinney et al. Each of these devices is constructed to dispense, in the manner of a vending machine, filled pharmaceutical prescriptions to patients (or representatives of patients). The machines are positioned such that one side is accessible from within a secure area of a pharmacy, where it can be loaded by a pharmacist or technician, and the other side is accessible from a non-secure area of the pharmacy, where patients can retrieve prescriptions. Typically, the patient must provide some identifying information, such as a credit card, an ID card, or the like, to prove his/her identity and/or authorization for retrieving the prescription, and also typically provides payment at that time. Ordinarily, these machines are controlled by a controller that is either embedded in or connected with the pharmacy's overall pharmacy management system.

It may be desirable to further advance the development and capability of pharmaceutical delivery systems.

SUMMARY OF THE INVENTION

As a first aspect, embodiments of the present invention are directed to a system for dispensing a plurality of customized doses of pharmaceuticals. The system comprises: a housing; a customer interaction station; a customized packaging station configured to selectively package individual doses of medication into customized packaging, the medications being selected responsive to input from the customer input station; and a controller connected to the customer interaction station and the customized packaging station, the controller configured to control the customized packaging based on customer input from the customer interaction station.

As a second aspect, embodiments of the present invention are directed to a system for dispensing medical products, comprising: a housing; a customer interaction station, the customer interaction station configured to receive requests for medical products stored in and dispensed from the housing; and a controller connected with the customer interaction station. The controller comprises: an inventory monitoring module configured to monitor inventory of medical products stored in and dispensed from the housing; and an alternate location module associated with the customer input station, the alternate location module configured to suggest alternative locations for systems that contain medical products that are absent from the housing. As a third aspect, embodiments of the present invention are directed to a system for dispensing regulated medications, comprising: a housing; a customer interaction station comprising a pharmaceutical dispensing station and a customer identification device configured to receive (a) customer-specific data input from the customer and (b) photographic or biometric input from the customer; and a controller connected with the customer interaction station. The controller comprises a regulated substances module that includes data associated with approval of customers to receive regulated substances and is configured to: receive the customer-specific data input and the photographic or biometric input; identify a customer corresponding to the customer-specific data; compare the identity of the customer corresponding to the customer-specific data input to the customer identified by the photographic or biometric input; and determine whether the identified customer is approved to receive a requested regulated substance. The system further comprises a drug verification station configured to verify the identity of the regulated medication.

As a fourth aspect, embodiments of the present invention are directed to a method for dispensing a plurality of individualized doses of pharmaceuticals grouped by administration time (e.g., time of day, day of the week, etc.). The method comprises: providing a customer interaction station; receiving a customer order for a medication via the customer interaction station; and dispensing selectively packaged individual doses of medication in customized packaging, the medications being selected responsive to input from the customer interaction station.

As a fifth aspect, embodiments of the present invention are directed to a method of dispensing medical products in a system for dispensing same, comprising: receiving via a customer interaction station a request for a medical product; and if the medical product is unavailable in the system, providing information regarding alternative locations that have the requested product in stock, the information being provided via the customer interaction station.

As a sixth aspect, embodiments of the present invention are directed to a method of dispensing regulated substances from a system for dispensing same, comprising: receiving, via a customer interaction station, customer-specific data input that identifies a customer; receiving, via the customer interaction station, photographic or biometric input that identifies a customer; receiving, via the customer interaction station, a request for a regulated substance; comparing the identity of the customer corresponding to the customer specific data to the customer identified by the photographic or biometric input; determining whether the identified customer is approved to receive the requested regulated substance; dispensing the regulated substance to the customer responsive to a positive determination and a positive comparison from a dispensing station; and automatically verifying the identity of the regulated substance prior to dispensing of the regulated substance from the dispensing station.

As a seventh aspect, embodiments of the present invention are directed to a system for dispensing pharmaceuticals, comprising: a housing; a customer interaction station that includes: a dispensing station for dispensing pharmaceuticals; and a display device for displaying information for a customer responsive to input from the customer interaction station; and a controller connected to the customer interaction station having a transaction module configured to select the displayed information responsive to customer input.

DETAILED DESCRIPTION OF EMBODIMENTS OF THE INVENTION

Figure 1:
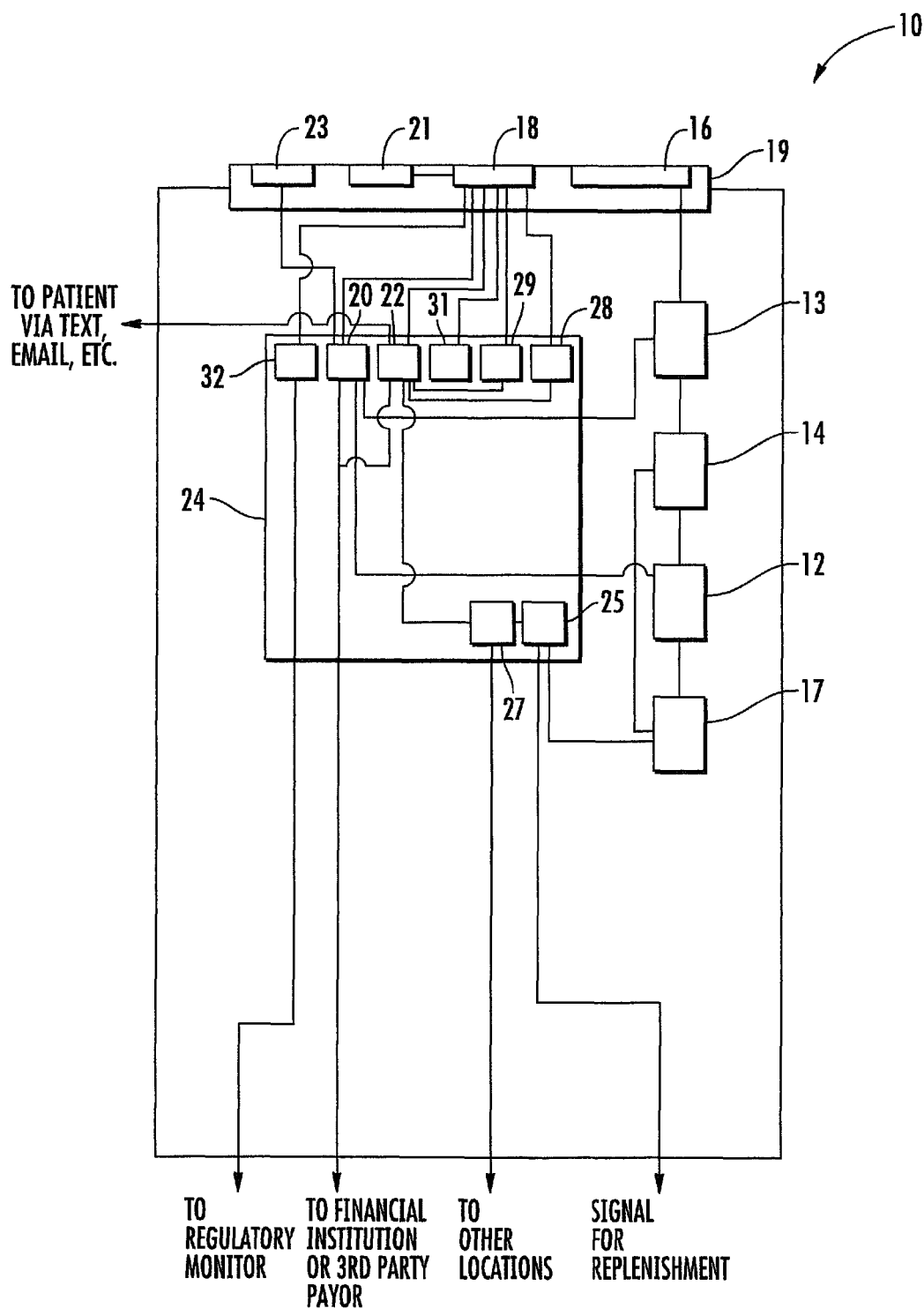
FIG. 1 is a schematic illustration of a system for dispensing pharmaceuticals and other medical items according to embodiments of the present invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Some embodiments may be embodied in hardware (including analog circuitry and/or digital circuitry) and/or in software (including firmware, resident software, micro-code, etc.). Consequently, as used herein, the term "signal" may take the form of a continuous waveform and/or discrete value(s), such as digital value(s) in a memory or register. Furthermore, various embodiments may take the form of a computer program product on a computer-usable or computer-readable storage medium having computer-usable or computer-readable program code embodied in the medium for use by or in connection with an instruction execution system. Accordingly, as used herein, the terms "circuit" and "controller" may take the form of digital circuitry, such as a logic gate array and/or computer-readable program code executed by an instruction processing device(s) (e.g., general purpose microprocessor and/or digital signal processor), and/or analog circuitry. Although some of the diagrams include arrows on communication paths to show a primary direction of communication, it is to be understood that communication may occur in the opposite direction to the depicted arrows. Well-known functions or constructions may not be described in detail for brevity and/or clarity.

Turning now to the drawings, a kiosk 10 is schematically illustrated in FIG. 1. As used herein, a "kiosk" is intended to include a customer-accessible structure, device or machine that can be located in any location or environment (for example, a pharmacy, a mass transit location, a retail location, a place of employment, a drive-up kiosk, a hotel, an airport, or the like) where a customer, patient, etc., can access it to purchase and retrieve medications and related supplies. Hereinafter, the term "kiosk" will be used to refer to such an apparatus, with the understanding that this term is intended to cover machines and other devices that fit the description above, including both free-standing structures and devices built into one or more walls, such as that of a pharmacy or the like. The kiosk may be climate-controlled for storage of sensitive drugs and to improve the shelf-lives of certain drugs. The kiosk may be placed in indoor or outdoor locations. Because it may contain pharmaceuticals, protected health information, money and/or credit card information, it should be formed of a sturdy construction and may be monitored by security cameras and armed with audible or visible alarm systems and may be securely mounted to its location. The kiosk 10 may include appropriate power and communication connections that enable the customer to employ any of a variety of systems/functions (such as pill counting and/or packaging) to deliver the required medication and information as well as to facilitate replenishment. The kiosk 10, either directly or through a centralized or decentralized network or other method, may also be able to store and analyze customer data.

As can be seen in FIG. 1, the kiosk 10 may include various stations and components for operation. Exemplary components include a customer interaction station 19 that has a graphic user interface (GUI) 18 and a dispensing station 16 for dispensing the medications to a customer, a pill counting station 12 for counting pills and depositing counted pills into an appropriate container (such as a vial), an inventory 17 of prepackaged drugs, a packaging station 13, a drug verification station 14 for verifying the identity of the medication to be dispensed, and a controller 24 that controls the activities of the kiosk 10 and provides communications with external sources and recipients. In some embodiments, the controller 24 is present within the kiosk 10, while in other embodiments the controller 24 is located remotely from the kiosk 10. The components identified above are discussed in greater detail below.

Referring again to FIG. 1, the pill counting station 12 may store, count and/or deliver drugs, medications and/or supplies to a customer. Such items may be stored in the inventory 17, or may be stored in the pill counting station 12. Medications may include patient specific or non-patient specific prescription or over-the-counter medications/drugs (OTC), including controlled OTC drugs such as pseudoephedrine. In some embodiments, the kiosk may have the ability to validate/authorize the purchase of controlled OTC drugs (for example, products containing ephedrine, pseudoephedrine, and phenylpropanolamine) by capturing customer-specific data such as a driver's license scan, biometric data, personal ID number, etc. and accessing public and private networks and databases to assist with verification. One example of a drug dispensing system exhibiting these capabilities is described in U.S. Patent Publication No. 2007/0043469 to Draper (this patent publication and all other patents and patent publications cited herein are hereby incorporated by reference in their entireties).

The pill counting station 12 may be able to count specific dosages of medications, such as a prescribed or requested number of pills or tablets, either in advance of or upon a customer request, via the pill counting station 12. The pill counting station 12 may take any number of forms known to be suitable for counting pharmaceutical pills, tablets, capsules and the like. Exemplary pill counting stations are discussed in U.S. Pat. No. 6,971,541 to Williams et al.; U.S. Pat. No. 7,344,049 to Daniels et al.; U.S. Pat. No. 7,014,063 to Shows et al; U.S. Pat. No. 4,869,394 to Hurst. Pill counting technologies that may be used in such stations are discussed in these same patents as well as U.S. Pat. No. 6,631,826 to Pollard et al. Exemplary systems for the customized packaging of products, as discussed below, are described in U.S. Pat. No. 7,258,248 to Kim which describes an additional type of counting technology useful in such a station; see also Pac-Med™ systems, available from Parata Systems, LLC, Durham, N.C.

Medications may be in any form in customized, patient specific quantities; exemplary forms of medication include oral dose solid, liquid, unit of use, transdermal patch, and the like. The kiosk 10 may also store and deliver ancillary products such as medical supplies (e.g. syringes), packages of tissues, cotton swabs, bandages, etc (typically stored in the inventory 17), and/or optometric products, such as clear and colored contact lenses and solutions for same, and eyeglasses (in some embodiments, the kiosk 10 may have the capacity to custom-produce lenses). The kiosk 10 may also store and deliver other medical products, such as "behind the counter" (BTC) drugs (medications distributed to customers upon a pharmacist's discretion, eliminating the need for a physician's prescription), "nutriceuticals" (e.g., vitamins and mineral supplements, nutritional supplements, herbal remedies, and the like), and/or drugs that require the existence of a particular condition or for the customer to meet particular criteria before being sold (e.g., the customer may need to show a blood pressure test prior to receiving an OTC or BTC blood pressure medication).

Referring again to FIG. 1, the drug verification station 14 can positively identify through one or more non-destructive analyses (for example, optical, near infrared, MRI, x-ray, Raman, etc.) the chemical and visual properties of any medication and positively identify that the correct medication is delivered. Exemplary drug verification systems include: optical systems which use pill characteristics such as color, shape, size, and surface features to identify drugs (e.g. U.S. Pat. No. 6,535,637 to Wootton et al.); systems which use various forms of spectroscopy, possibly in combination with optical systems, such as those described in U.S. Pat. No. 6,771,369 to Rzasa et al. (Near-Infrared spectroscopy); U.S. Pat. No. 7,218,395 to Kaye et al (Raman spectroscopy/multimodal multiplex spectroscopy); and U.S. Pat. No. 7,154,102 to Poteet et al. (fluorescence spectroscopy); and U.S. Patent Application Publication No. 2008/0183410 to Klein et al. (Raman spectroscopy); and systems that use more than one sensor (any of a variety of spectrometers including Near-infrared, Raman, dielectric, acoustical; optical sensors such as cameras; weight sensors such as scales; e-field sensors, etc.) discussed in U.S. Patent Application Publication No. 2006/0124656 to Popovich, Jr. This verification capability may be present for any form of the medication, such as solid, liquid, transdermal patch, or the like, and/or form of packaging, including unit dose, multi-dose, vial, bingo card packaging, etc. Additionally, the verification system may be able to verify the identity of several different drugs within the same package (such as for customized packaging of medications, as discussed below) and that the correct number of doses of each drug is contained with the package being dispensed. The drug verification station 14 may also include the ability to scan barcodes or RFID tags or otherwise detect identifying indicia on prepackaged drugs to confirm the identity of the drug.

Referring once again to FIG. 1, the packaging station 13 may package products in a number of forms in the packaging station 13. For example, the systems of the packaging station 13 may be able to handle and count medications either in bulk form or any of a variety of pre-packaged formats, such as blister packaging, strip packaging, "bingo card" packaging, and the like. If in bulk form, the packaging station 13 may be able to count and dispense in unit packaging, multi-dose packaging, vials, etc. If in pre-packaged form (for example, blister, manufacturer or retail package), the packaging station 13 may be able to deliver the entire pre-packaged product and/or subdivide the pre-packaged product to meet customers' requests. The packaging station 13 may also be capable of delivering medications to customers in single dose packages (pouch, strip, sachet, blister-packs, etc,), multi-dose packages, vials, bottles, bingo card packaging or the like.

The packaging station 13 may be configured such that packages can be customized for specific customers based on input from the customer, with the ability to custom-label the package(s) for a specific customer. Exemplary systems demonstrating various aspects of the process involved in preparing customer-specific customized packaging are found in U.S. Pat. No. 6,216,418 to Kim; U.S. Pat. No. 6,585,132 to Kim; U.S. Pat. No. 6,898,919 to Kim; U.S. Pat. No. 7,028,447 to Sung; U.S. Pat. No. 7,059,098 to Kim; and U.S. Pat. No. 7,331,151 to Kim. For example, one or more pouches may be dispensed to the customer, wherein each pouch contains a single dose of one or more medications, with pertinent information including instructions for taking the medication printed on the pouch. The customer may receive a sufficient number of pouches/doses to span a specific time period: for example, all dosages in a regimen of antibiotic therapy, sufficient doses of a specific medication to last a customer for the duration of a trip, a month's supply of vitamins, etc. Each pouch may contain all medications to be taken at a certain time of day (e.g., breakfast, before bed, etc.) to simplify the medication administration process for the customer. Alternatively, each pouch may contain all medications to be taken by the customer on a particular day or in any particular time period, or the organization of the medication into the pouches may be customized in a way devised by the customer. Each pouch may contain a combination of prescription and non-prescription medications as available in the kiosk 10 and may be chosen by the customer.

The packaging station 13 may also be capable of applying a label to dispensed packages. Label information may be customized for a specific customer and can include (but is not limited to) customer name, medication type (or types, for customized pouch packaging of multiple medications or the like), expiration date, manufacturer and/or lot number, dosage, dosage time, drug warnings and interaction information, reminders, logos, date, location of dispensing, prescribing physician, numbering of packages, indicator of remaining doses, etc. See, e.g., U.S. Pat. No. 6,892,780 to Vollm et al., U.S. Patent Application Publication No. 2008/0110555 to Pollard et al.; U.S. Patent Publication No. 2005/0049746 to Rosenblum for various approaches to labeling of prescription packages.

Continuing to refer to FIG. 1, the customer interaction station 19 includes the GUI 18, the dispensing station 16, a transaction device 23, and one or more customer identification device 21. The dispensing station 16 may take the form capable of dispensing medications to customers via customer information input via the GUI 18. Prescription medications can be dispensed via a number of mechanisms; exemplary devices for dispensing are described and illustrated in U.S. Pat. No. 7,228,200 to Baker et al.; U.S. Pat. No. 6,766,218 to Rosenblum; U.S. Pat. No. 7,123,989 to Pinney et al.; and U.S. Patent Publication Nos. 2005/0021175 to Bain and 2007/0043469 to Draper.

Referring again to FIG. 1, the GUI 18 (for example, a touch screen display, a keypad, or the like) enables a customer to operate the kiosk 10. In some embodiments, another customer input device (such as a telephone or speaker/microphone combination) may also be included. The GUI 18 may include a series of menus that allow the customer to select a language for interaction with the system, request information, order products, or perform transactions. For example, in response to queries from the system the customer may enter symptoms that he/she is experiencing and a diagnostic module 31 of the controller 24 may recommend medication(s) and dosage schedule based on symptoms and/or customer specific data, such as described in U.S. Pat. No. 5,299,121 to Brill et al. and PCT Application No. PCT/US01/14209. The customer may also enter symptoms, conditions, and/or medications currently being taken and request a suggested product (for example, a person suffering from lethargy and currently taking a cold medicine may seek a therapeutic vitamin combination, or the system may recommend vitamins or other nutraceuticals to supplement a customer's medication regimen). The customer may also directly select any non-prescription product in any combination (such as a particular cold medication, allergy medication, gastrointestinal treatment, headache medication, etc.). In either case, the customer may elect that the packaging form includes labeling. The customer may also select a prescription product as a refill of an existing prescription for the patient (the customer may or may not be the patient). In this case, the system may check available databases to determine if the refill is authorized or contact the customer's physician for authorization to provide the prescription refill.

The GUI 18 may also be employed to present to the customer advertisements and promotional materials provided by the promotions module 29 of the controller 24. The customer interaction station 19 may also provide coupons and/or credit for items, particularly any items that are not available from a specific machine. The advertisements, promotional materials and/or coupons may be customized to the customer, based on previous transactions on the system and/or information about that customer that is stored in the system or accessed by the system, such as medical records, prescription history, etc.

In addition to the GUI 18, which enables a customer to operate the kiosk 10, the customer interaction station 19 may include one or more electronic or other displays for interactive content (for example, educational) via the communications module 22, promotional content (for example, advertisements) via the promotions module 29, or for other uses.

Still referring to FIG. 1, a transaction device 23 of the customer interaction station 19 may be able to accept a variety of payment options such as cash, check, credit/debit cards, employee/employer-specific payment cards/methods, RF payment via a fob, cell phone, etc. A customer identification device 21 is also present in the customer interaction station 19 and is configured to be capable of identifying and authorizing customers to perform transactions. Customer recognition may be based on a customer-specific data input (such as a personal ID number, social security number, or the like, any or all of which may be included on a magnetic stripe or a card), biometric data, photograph/facial recognition or another identifying method or combination of methods.

Still referring to FIG. 1, the controller 24 includes a number of modules for assisting with operation of the kiosk 10, including a transaction module 20, a communications module 22, an inventory monitoring module 25, an alternate location module 27, a signaling module 28, a promotions module 29, a diagnostic module 31, and a regulated substances module 32. The transaction module 20 is connected with the transaction device 23 and oversees the purchase of items from the kiosk 10, including contacting financial institutions as needed. Also, the transaction module 20 may be configured to deliver, directly to the customer, a transaction receipt/record, a medical guide (that may include descriptions of and warnings for products delivered) and any other information or records necessary or desirable to complete the transaction or satisfy laws or regulations. The transaction module 20 may also be configured to automatically communicate with insurance companies to perform adjudication for prescription transactions or with flexible spending account management companies for approval of prescription or other transactions.

The transaction module 20 may also provide analysis of customer transactions. For example, the transaction module 20 may have the ability to recognize customers via the customer-specific code, biometric data or other identifying method and, upon such recognition, recall the customer's ordering history. This can enable the kiosk 10, via the GUI 18, to recommend products via the promotions module 29 or the diagnostic module 31 (although this is not necessary to use the kiosk 10) and/or deliver coupons or other promotional material via hard copy print-out or electronic means (for example, via e-mail, text messaging, fax, etc.) in connection with the promotions module 29. Upon return visits, the kiosk 10 may also remind a customer of what he/she previously purchased, even if a customer uses a kiosk 10 in a different physical location. The kiosk 10 or a monitoring center may also be organized to remind a customer, via E-mail, text message, automated phone call, or the like, that a prescription has run out and/or that a refill is needed, to help promote patient adherence/compliance and/or alert a customer to other promotional or relevant facts.

Still referring to FIG. 1, the communications module 22 may be configured to enable the kiosk 10 to be capable of two-way communications with customers, service personnel, replenishment personnel, etc. Communication may be achieved via multiple media including, but not limited to, pagers, cell networks, wireless networks, machine-to-machine networks and protocols, the Internet and any other form of wireless or wire line communication method. The communications module 22 may also be configured to receive electronic prescriptions (eRx) from physicians and send outbound notifications and requests to physicians, insurance companies or other payors, and patients/customers. Communication of eRx from a physician to a kiosk 10 may be of particular advantage if the customer is traveling and has forgotten his/her prescription medication; a temporary supply can be provided from a kiosk 10 upon receipt from the physician of an eRx, perhaps providing for only sufficient medication to last until the customer returns home. Initiation of an eRx could occur by request of the customer while at a kiosk, or may be otherwise initiated such as via a phone call or visit to the physician. When the eRx is received from the physician, the system can identify a kiosk that has the medication in supply and is in a desired location for the customer. For example, the system may identify a kiosk within a defined radius from a particular airport or hotel, if the customer is traveling, or within a defined radius from the customer's home or work address, if the customer is not traveling but needs to obtain the medication from a kiosk (after pharmacy hours, greater convenience, etc.). The system may then reserve the medication at that kiosk location to ensure that it is available for the customer when the customer comes to retrieve it, and may also send a notification (email, text message, automated phone call, or the like) to the customer to notify the customer of the location of the kiosk where the medication has been reserved. The notification to the customer may include any relevant information such as address of the kiosk location, directions to the kiosk, hours of operation of the facility where the kiosk is housed, etc.

Communications to physicians may also include requests to approve certain substitutions, such as generics, for a particular prescription. In such instances, as well as other instances such as communications with insurance companies or other payors, the communications may involve receipt of information by the communications module 22, such as approval for substitution, approval of payment, etc. The communications module 22 may also be configured to communicate with appropriate databases housing electronic health records and/or prescription history of the patient in order to use such information in the determination of the appropriate medication for the patient's symptoms or review the prescription history for possible drug interactions with any medications to be dispensed.

In addition, the communications module 22 may enable the kiosk 10 to communicate, via the alternate location module 27, with other machines (machine-to-machine communication referred to as "MTM"), a monitoring center and/or service personnel for product replenishment notification (including information such as drug type and amount needed), service requests, updates, warnings, pricing and promotional updates, etc. Promotional updates, coupons and advertising may be managed regionally and/or seasonally, with such management occurring remotely via a content server. For example, in the spring season, advertisements or promotional materials may highlight allergy medications, while during the winter months, cold and flu medications may be the focus. Also, during the winter months, cold and flu medications may be the focus of advertising or promotional materials in certain geographical regions such as the northeast U.S., while allergy medications still may be promoted/advertised in other areas such as the southern regions of the U.S. The communications module 22 may also be capable of soliciting interest in or registering participants for clinical trials, either for all customers or for customers meeting a particular therapeutic profile.

The communications module 22 may be able to send outbound messages to a customer's cell phone, e-mail address, text messaging, etc, for a variety of notification purposes such as pick-up reminders, sales promotions, etc. The communications module 22 may also be able to access appropriate information networks for such things as insurance adjudication and identification verification (for example, for pseudoephedrine purchases), some of which is described in U.S. Patent Publication Nos. 20080086326 to Moura et al. and 2008/0269947 to Beane et al.

The communications module 22 may also be able to access centralized or distributed service networks for any maintenance operations such as software or information updates, service updates and status, remote monitoring, review for potential drug interaction, prescriptions overdue for pick-up, etc. See, e.g., U.S. Pat. No. 7,093,755 to Denenberg et al.

Still referring to FIG. 1, the inventory monitoring module 25 may also be configured to monitor the replenishment needs of the kiosk 10. More specifically, the inventory monitoring module 25 may be capable of notifying a monitoring center or directly notifying service personnel that the kiosk 10 needs replenishment of one or more products, materials for packaging of products, labels, etc. The inventory monitoring module 25 may be capable of indicating the specific items that need to be replenished so that service personnel may plan the service trip accordingly and ensure availability of the materials to be replenished. Also, if the kiosk 10 is out of a particular product, the inventory monitoring module 25 may also be configured to inform a customer of a nearby kiosk location that offers that product and has it available for dispensing. The inventory monitoring module 25 of the kiosk 10 that has available product may also reserve the requested amount of the drug for that customer to ensure that it remains available with the customer arrives to pick it up. The kiosk 10 may also send a notification (email, text message, automated phone call, or the like) to the customer to notify the customer of the location of the kiosk where the medication has been reserved. The inventory monitoring module 25 may further be capable of notifying the monitoring center or service personnel of any maintenance or service needs such as jammed or otherwise inoperable dispensers, requirements for collection of cash or stocking of change, periodic cleaning or preventative maintenance of drug dispensing units, etc.

Upon notification of the need for replenishment of drug products or other supplies by the inventory monitoring module, the monitoring center and/or service personnel may then initiate procedures for replenishment of the kiosk. Such replenishment of a kiosk requiring same may be done by manual restocking of individual items by service personnel upon arrival, or replenishment may be performed in a more automated fashion, such as that described in U.S. Patent Publication No. 2009/0005905, the disclosure of which is hereby incorporated herein in its entirety. Items to be restocked in a particular kiosk system may be loaded into a storage bin, canister, reel, cartridge, magazine or the like at a central stocking facility; the storage bin, of a shape and size compatible with the design of the kiosk, is capable of holding multiple units of items stocked in the kiosk. Service personnel may deliver the storage bin to the specified kiosk and install the storage bin in the unit. The kiosk may then perform a self-replenishment routine where items are removed from the storage bin by a robotic arm in the kiosk and placed in the appropriate location in the kiosk for later retrieval and delivery to a customer. The system may make use of labels on the items (bar code, RFID, etc.) which it may scan to confirm identification of the item upon removal from the storage bin and notification to the system of the location of the item once it is stocked in the kiosk. Alternatively, items to be restocked may be loaded into a shelf, bin, canister, reel, cartridge, magazine or other appropriate storage unit, depending on the configuration of the kiosk, and the storage unit loaded directly into the kiosk in an appropriate location. The loading of the storage unit may coincide with the removal of empty or partially empty storage units. The storage units may contain labels, such as bar codes or RFID tags, containing information regarding the contents of the unit. The kiosk system may then scan the label and use the information to update its inventory as well as notify the controller of the location of the items for delivery to customers.

For the dispensing of substances controlled by Drug Enforcement Agency or other federal, state or local regulations (at present, products containing ephedrine, pseudoephedrine, and phenylpropanolamine), the kiosk 10 may include hardware and/or software (for example, in the form of the regulated substances module 32) that can enable the system to identify and serve customers that place requests for controlled substances. DEA regulations require that the pharmacist follow certain procedures when presented with a request for a controlled substance, may also require that the purchaser be listed in a log book, and may also set upper limits on sales on a daily and/or monthly basis, both for individual customers and for pharmacy locations. The regulated substances module 32 may have the ability to maintain records of amounts of controlled substances dispensed and to transmit the information to the appropriate federal, state and/or local authorities. The regulated substances module 32 may record electronic signatures required for the purchase of controlled substances and access appropriate database(s) for the authorization of the signature before release of the product to the customer.

Figure 2:
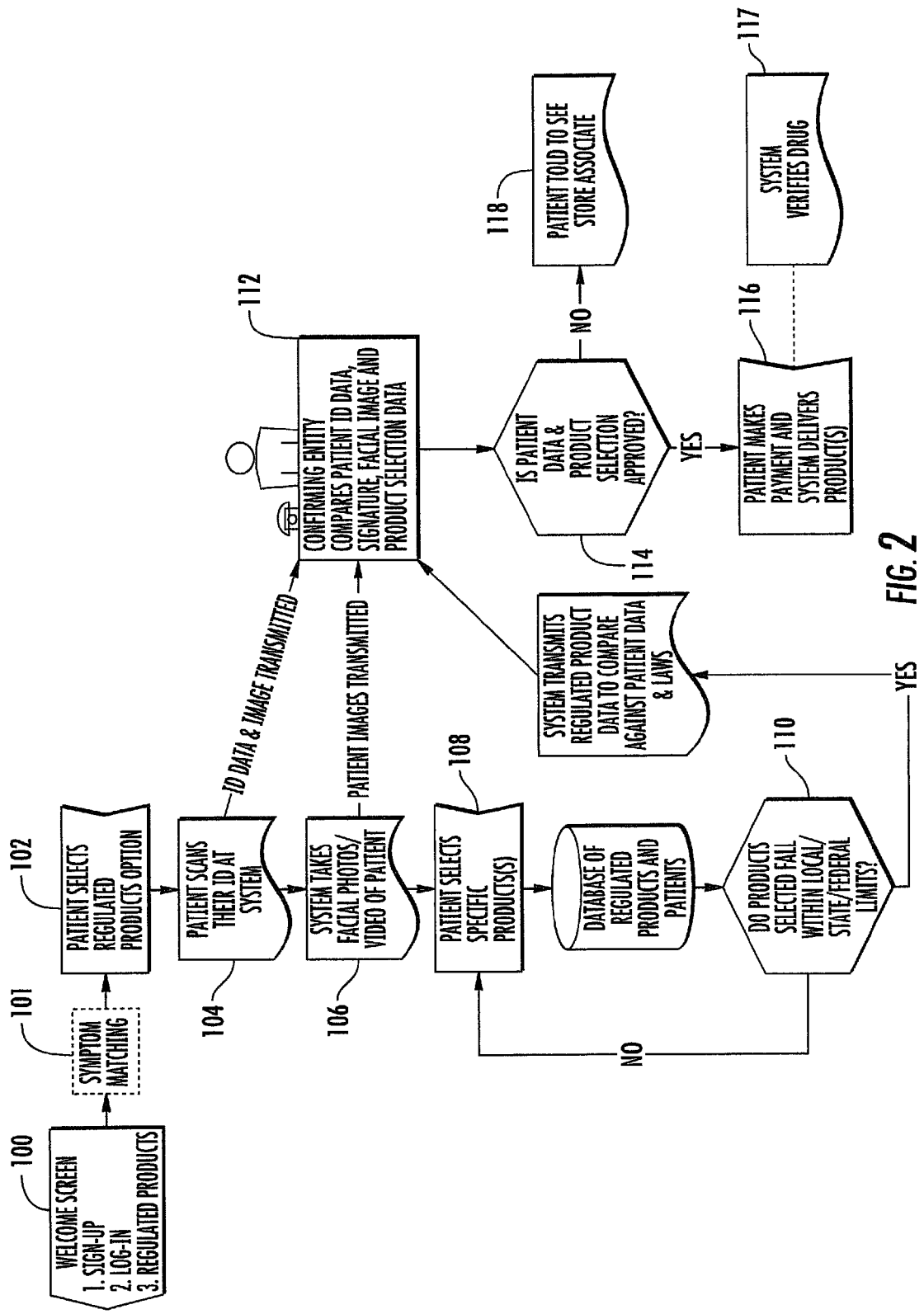
FIG. 2 is a schematic illustration of a portion of the system of FIG. 1 that enables the sale of controlled prescription medications.

An exemplary method for addressing the DEA regulations with a kiosk having a regulated substances module 32 such as that discussed above is illustrated in FIG. 2. As shown in FIG. 2, the GUI 18 of the kiosk 10 may include a menu that has as an option "regulated products" (Block 100). An optional feature includes the matching of patient symptoms to a recommended product (Block 101). If the customer selects the regulated products option (Block 102), the customer scans an ID card (Block 104) that identifies the customer to the system (if the customer does not select a regulated product, the system proceeds to payment as shown in Block 103). The ID card may be a smart card or RFID tag that maintains a record of information such as the patient's medical history, prescription history and current status, and information regarding transactions at that or other kiosks on the network. The smart card or RFID tag would be read/writable so that information from the current transaction may also be recorded. The identification data of the customer is transmitted to an ID verification station. The system also takes a photo of the face of the customer or acquires other customer identification data (such as biometric data) (Block 106) and transmits the photographic data to the ID verification station. The customer then selects a specific product for dispensing (Block 108). The system queries whether the selected products are regulated (Block 110) by comparing the related product to an existing database. If the product is not regulated, the system returns the customer to the menu at Block 108 that allows the selection of additional product(s), if desired. If the product is regulated, the system transmits the product data to the ID verification station.

At the ID verification station, a comparison between the customer ID and the photographic or biometric data of the customer is performed to confirm that the customer requesting the medication matches the identity of the person listed on the ID card (Block 112). If photographic data is employed, the comparison can be performed manually, or can be performed by an automated photographic image comparator. If biometric data is employed, the comparison can be performed manually or by a suitable automated unit. Manual comparison of either the photographic or biometric data can be performed by a pharmacist or other agent of the retailer. Such an individual may be located at the same geographic location as the kiosk, if the kiosk is located in a pharmacy or other location where such an individual may be available in person. Alternatively, the individual may be located remote from the kiosk with all of the necessary information communicated electronically; for example, a single individual could serve as the source for manual confirmation for a plurality of kiosk locations. Regardless of whether they are near or remote, a person would perform the identity confirmation for the system prior to proceeding with the dispensing process. If the customer's ID card matches the identity of the customer (as determined by the photographic or biometric data and confirmation of the match from the system, performed automatically, or from the individual performing the manual verification), the system then inquires whether the customer is approved for the dispensing of the product selected at Block 108 by the customer (Block 114). If the customer is approved, the system can dispense the product, receive payment, etc. as described above in connection with FIG. 1 (Block 116). In some embodiments, the drug is verified at the drug verification station (Block 117). If the customer is not approved, he or she may be directed to contact a pharmacy associate or the like (Block 118).

FIGS. 1 and 2 illustrate the architecture, functionality, and operations of embodiments of hardware and/or software according to various embodiments of the present invention. It will be understood that each block of the flowchart and/or block diagram illustrations, and combinations of blocks in the flowchart and/or block diagram illustrations, may be implemented by computer program instructions and/or hardware operations. In this regard, each block represents a module, segment, or portion of code, which comprises one or more executable instructions for implementing the specified logical function(s).

It should be noted that, in other implementations, the function(s) noted in the blocks may occur out of the order noted in FIGS. 1 and 2. For example, two blocks shown in succession may, in fact, be executed substantially concurrently, or the blocks may sometimes be executed in the reverse order, or the blocks may be separated by one or more additional steps, depending on the functionality involved. These computer program instructions may be provided to a processor of a general purpose computer, a special purpose computer, or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer usable or computer-readable memory that may direct a computer or other programmable data processing apparatus to function in a particular manner, such that the instructions stored in the computer usable or computer-readable memory produce an article of manufacture including instructions that implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart and/or block diagram block or blocks.

The foregoing embodiments are illustrative of the present invention, and are not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of dispensing regulated substances from a system for dispensing same, comprising:

receiving, via a customer interaction station, customer-specific data input that identifies a customer;

receiving, via the customer interaction station, photographic or biometric input that identifies a customer;

receiving, via the customer interaction station, a request for a regulated substance;

comparing the identity of the customer corresponding to the customer-specific data to the customer identified by the photographic or biometric input;

determining whether the identified customer is approved to receive the requested regulated substance;

dispensing the regulated substance to the customer responsive to a positive determination and a positive comparison from a dispensing station; and automatically verifying the identity of the regulated substance prior to dispensing of the regulated substance from the dispensing station.

2. The method defined in claim 1, wherein the comparing step is performed by the controller.

3. The method defined in claim 1, wherein the comparing step is performed manually.

\* \* \* \* \*